US012076092B2

(12) United States Patent
Popovic et al.

(10) Patent No.: US 12,076,092 B2
(45) Date of Patent: *Sep. 3, 2024

(54) SINGLE-PORT SURGICAL PROCEDURE USING IMAGE GUIDED ARTICULATED ROBOT

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 260 days.

This patent is subject to a terminal disclaimer.

(21) Appl. No.: 17/579,752

(22) Filed: Jan. 20, 2022

(65) Prior Publication Data

US 2022/0175465 A1 Jun. 9, 2022

Related U.S. Application Data

(63) Continuation of application No. 15/762,365, filed as application No. PCT/IB2016/055519 on Sep. 16, 2016, now Pat. No. 11,259,876.

(Continued)

(51) Int. Cl.
*A61B 34/20* (2016.01)
*A61B 1/00* (2006.01)
(Continued)

(52) U.S. Cl.
CPC .......... *A61B 34/20* (2016.02); *A61B 1/00149* (2013.01); *A61B 1/045* (2013.01);
(Continued)

(58) Field of Classification Search
CPC ..... A61B 18/02; A61B 18/04; A61B 1/00149; A61B 1/045; A61B 2018/00172;
(Continued)

(56) References Cited

U.S. PATENT DOCUMENTS 8,221,402 B2 7/2012 Francischelli
8,273,081 B2 9/2012 Viswanathan
(Continued)

FOREIGN PATENT DOCUMENTS

WO 2013026012 A1 2/2013
WO 2015118423 A1 8/2015

OTHER PUBLICATIONS

Ota, Takeyoshi et al "Epicardial Atrial Ablation Using a Novel Articulated Robotic Medical Probe via a Percutaneous Subxiphoid Approach", Innovations, vol. 1, No. 6, 2006.

(Continued)

*Primary Examiner* — Brooke Labranche

(57) ABSTRACT

A robotic surgical system employing a treatment catheter (30) (e.g., a thermoablation catheter or a cyroablation catheter), and an articulated robot (40) including a plurality of linkages and one or more joints interconnecting the linkages for navigating the treatment catheter (30) within an anatomical region. The robotic surgical system further employs a robot controller (41) for controlling a navigation by the articulated robot (40) of the treatment catheter (30) along a intraoperative treatment path within the anatomical region relative to the anatomical structure derived from a planned treatment path within the anatomical region relative to the anatomical structure based on a registration between the articulated robot (40) and a preoperative image (21a) illustrative of the planned treatment path within the anatomical region relative to the anatomical structure.

13 Claims, 7 Drawing Sheets

Related U.S. Application Data

(60) Provisional application No. 62/233,636, filed on Sep. 28, 2015.

(51) Int. Cl.

| | |
|---|---|
| *A61B 1/045* | (2006.01) |
| *A61B 18/02* | (2006.01) |
| *A61B 18/04* | (2006.01) |
| *A61B 34/00* | (2016.01) |
| *A61B 34/10* | (2016.01) |
| *A61B 34/30* | (2016.01) |
| *A61B 34/32* | (2016.01) |
| *A61B 6/00* | (2006.01) |
| *A61B 6/12* | (2006.01) |
| *A61B 18/00* | (2006.01) |

(52) U.S. Cl.
CPC .............. *A61B 18/02* (2013.01); *A61B 18/04* (2013.01); *A61B 34/00* (2016.02); *A61B 34/10* (2016.02); *A61B 34/30* (2016.02); *A61B 34/32* (2016.02); *A61B 6/12* (2013.01); *A61B 6/5247* (2013.01); *A61B 2018/00172* (2013.01); *A61B 2018/00351* (2013.01); *A61B 2018/00577* (2013.01); *A61B 2018/00982* (2013.01); *A61B 2018/0212* (2013.01); *A61B 2034/107* (2016.02); *A61B 2034/2057* (2016.02); *A61B 2034/2059* (2016.02); *A61B 2034/2065* (2016.02); *A61B 2034/301* (2016.02); *A61B 2034/305* (2016.02); *A61B 2034/306* (2016.02)

(58) Field of Classification Search
CPC ........... A61B 2018/00351; A61B 2018/00577; A61B 2018/00982; A61B 2018/0212; A61B 2034/107; A61B 2034/2057; A61B 2034/2059; A61B 2034/2065; A61B 2034/301; A61B 2034/306; A61B 2034/305; A61B 34/10; A61B 34/00; A61B 34/20; A61B 34/30; A61B 34/32; A61B 6/12; A61B 6/5247
See application file for complete search history.

(56) References Cited

U.S. PATENT DOCUMENTS

| | | |
|---|---|---|
| 8,617,152 B2 | 12/2013 | Werneth |
| 8,641,710 B2 | 2/2014 | Doty |
| 8,696,658 B2 | 4/2014 | Pankratov |
| 8,965,496 B2 | 2/2015 | Bailin |
| 9,014,793 B2 | 4/2015 | Harley |
| 9,033,885 B2 | 5/2015 | Thapliyal |
| 2007/0083193 A1 | 4/2007 | Werneth |
| 2007/0299427 A1 | 12/2007 | Yeung |
| 2010/0114094 A1 | 5/2010 | Thapliyal |
| 2012/0004547 A1 | 1/2012 | Harks |
| 2012/0226145 A1 | 9/2012 | Chang |
| 2013/0103064 A1 | 4/2013 | Arenson |
| 2013/0282005 A1 | 10/2013 | Koch |
| 2013/0303883 A1 | 11/2013 | Zehavi |
| 2014/0022250 A1 | 1/2014 | Mansi |
| 2014/0343416 A1 | 11/2014 | Panescu |
| 2015/0119671 A1 | 4/2015 | Varma |
| 2015/0265344 A1 | 9/2015 | Aktas |
| 2016/0170427 A1 | 6/2016 | Baba |

OTHER PUBLICATIONS

Ota, Takeyoshi et al "A Novel Highly Articulated Robotic Surgical System for Epicardial Ablation", Conf. Proc. IEEE Eng. Medical Biology Society, 2009.
Wood, N.A. et al "Closed-Loop Control of Needle Steering for Percutaneous Kidney Access", 2010.
Neuzil, P. et al, Single-site Access Robot-Assisted Epicardial Mapping with a Snake Robot: Preparation and Wrst Clinical Experience, Journal Robotic Surgery, 2013.
Neuzil, P. et al "Single Port Subxiphoid Epicardial Ablation using Snake Robotic System" Journal Robotic Surgery, 2012.
Tully, Stephen et al "Shape Estimation for Image-Guided Surgery with a Highly Articulated Snake Robot", 2011.

SINGLE-PORT SURGICAL PROCEDURE USING IMAGE GUIDED ARTICULATED ROBOT

CROSS-REFERENCE TO PRIOR APPLICATIONS

This application is a Continuation of U.S. application Ser. No. 15/762,365, filed Mar. 22, 2018, which is the U.S. National Phase application under 35 U.S.C. § 371 of International Application No. PCT/IB2016/055519, filed on Sep. 16, 2016, which claims the benefit of U.S. Provisional Patent Application Ser. No. 62/233,636, filed on Sep. 28, 2015. These applications are hereby incorporated by reference herein.

FIELD OF THE INVENTION

The present disclosure generally relates to image guidance of an articulated robot during a minimally invasive procedure. The present disclosure more particularly relates to X-ray guidance of an articulated robot during a minimally invasive Cox-Maze procedure.

BACKGROUND OF THE INVENTION

Generally, a normal heartbeat involves a generation of an electrical impulse by a sinoatrial node in the right atrium that propagates through the atrium chambers causing the atrium chambers to contract and pump blood into the ventricular chambers. The electrical pulse further propagates from the atrium chambers to an atrioventricular node of the heart located between the atrium and ventricular chambers causing the ventricular chamber to fill with blood, and the further propagates from the atrioventricular node to the ventricular chambers causing the ventricular chambers to contract and pump blood through the blood vessels.

Atrial fibrillation is an abnormal heart rhythm whereby the regular electrical impulse is not generated by sinoatrial node causing abnormal propagation of an irregular electrical impulses from the upper chambers to the lower chambers resulting in an uncoordinated rhythm between the atrium and ventricular chambers. The Cox-Maze procedure as known in the art is a surgical procedure to treat atrial fibrillation by an ablation of the atrium chambers in a maze like pattern to block the irregular electrical impulses.

In a traditional Cox-Maze procedure, a sternotomy and rib spreading is required to access the atrium of the heart. Due to invasiveness of this procedure, traditional Cox-Maze procedure is rarely performed as a stand-alone treatment, and is usually done adjacent to other heart procedures, such as bypass or valve surgery. Minimally invasive procedures are designed to allow stand-alone Cox-Maze. However, due to the maze-like path of traditional rigid instruments, current implementation of a minimally invasive Cox-Maze procedure usually requires six (6) ports between the ribs due to complexity of ablation instrument path on the heart. Moreover, any robotic based minimally invasive Cox-Maze procedure involves human operation of the robot.

SUMMARY OF THE INVENTION

The present disclosure provides inventions utilizing an image guided dexterous robot for autonomously performing single-port minimally invasive procedures within an anatomical region (e.g., a thoracic region, a cranial region, an abdominal region, a dorsal region or a lumbar region), particularly an X-ray guided robot for autonomously performing a single-port minimally invasive Cox-Maze procedure within the thoracic region.

One form of the inventions of the present disclosure is a robotic surgical system for executing a procedural treatment of an anatomical structure within an anatomical region (e.g., a minimally invasive Cox-Maze ablation procedure of a heart within the thoracic region).

The robotic surgical system employs a treatment catheter (e.g., a thermoablation catheter or a cyroablation catheter), and an articulated robot including a plurality of linkages and one or more joints interconnecting the linkages. The articulated robot is for navigating the treatment catheter within the anatomical region.

The robotic surgical system further employs a robot controller for controlling a navigation by the articulated robot of the treatment catheter along a navigation by the articulated robot of the treatment catheter along an intraoperative treatment path within the anatomical region relative to the anatomical structure derived from a planned treatment path within the anatomical region relative to the anatomical structure based on a registration between the articulated robot and a preoperative image illustrative of the planned treatment path within the anatomical region relative to the anatomical structure.

Further, the articulated robot may be structurally designed to alternatively or concurrently navigate the treatment catheter and a camera catheter within the anatomical region.

A second form of the inventions of the present disclosure is a robotic surgical method for executing the procedural treatment of the anatomical structure within the anatomical region (e.g., a minimally invasive Cox-Maze ablation procedure of a heart within the thoracic region).

The robotic surgical method involves an imaging controller controlling an image registration between the preoperative image (e.g., a CT, MRI or US image of the thoracic region) and the articulated robot, wherein the preoperative image is illustrative a planned treatment path within an anatomical region relative to the anatomical structure.

Based on the registration by the imaging controller between the preoperative image and the articulated robot, the robotic surgical method further involves a robot controller controlling a navigation by the articulated robot of the treatment catheter along a intraoperative treatment path within the anatomical region relative to the anatomical structure derived from a planned treatment path within the anatomical region relative to the anatomical structure.

For purposes of the inventions of the present disclosure, terms of the art including, but not limited to, "treatment catheter", "camera catheter", "autonomous control", "image registration", "imaging modality", "preoperative image" and "intraoperative image" are to be interpreted as understood in the art of the present disclosure and as exemplary described herein.

For purposes of the inventions of the term "planned treatment path" broadly encompasses a delineation of a path for the treatment catheter within a preoperative image of an anatomical region for executing a planned treatment of an anatomical structure (e.g., a path planning for a minimally invasive Cox-Maze ablation procedure of a heart within the thoracic region as illustrated within the preoperative CT, MRI or US image), and the term "intraoperative treatment path" broadly encompasses a delineation of a path for the treatment catheter within the anatomical region for implementing the planned treatment path as controlled by the articulated robot.

For purposes of the inventions of the present disclosure, the term "articulated robot" broadly encompasses any robotic device structurally configured, entirely or partially, with motorized control of one or more joints (e.g., a pivot joint) serially connected with rigid linkages including a proximal linkage, a distal linkage and optionally one or more intermediate linkages.

For purposes of the inventions of the present disclosure, the term "controller" broadly encompasses all structural configurations of an application specific main board or an application specific integrated circuit housed within or linked to a workstation for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s).

Examples of the workstation include, but are not limited to, an assembly of one or more computing devices (e.g., a client computer, a desktop and a tablet), a display/monitor, and one or more input devices (e.g., a keyboard, joysticks and mouse).

For purposes of the inventions of the present disclosure, the term "application module" broadly encompasses a component of the controller consisting of an electronic circuit and/or an executable program (e.g., executable software and/firmware) for executing a specific application.

For purposes of the inventions of the present disclosure, any descriptive labeling of the a controller herein (e.g., a "robot" controller and an "imaging" controller) serves to identify a particular controller as described and claimed herein without specifying or implying any additional limitation to the term "controller".

Similarly, for purposes of the inventions of the present disclosure, any descriptive labeling of an application module herein (e.g., a "path planning control" module, a "registration control" module, a "transformation control" module, and an "image feedback control" module) serves to identify a particular application module as described and claimed herein without specifying or implying any additional limitation to the term "application module".

The foregoing forms and other forms of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1:
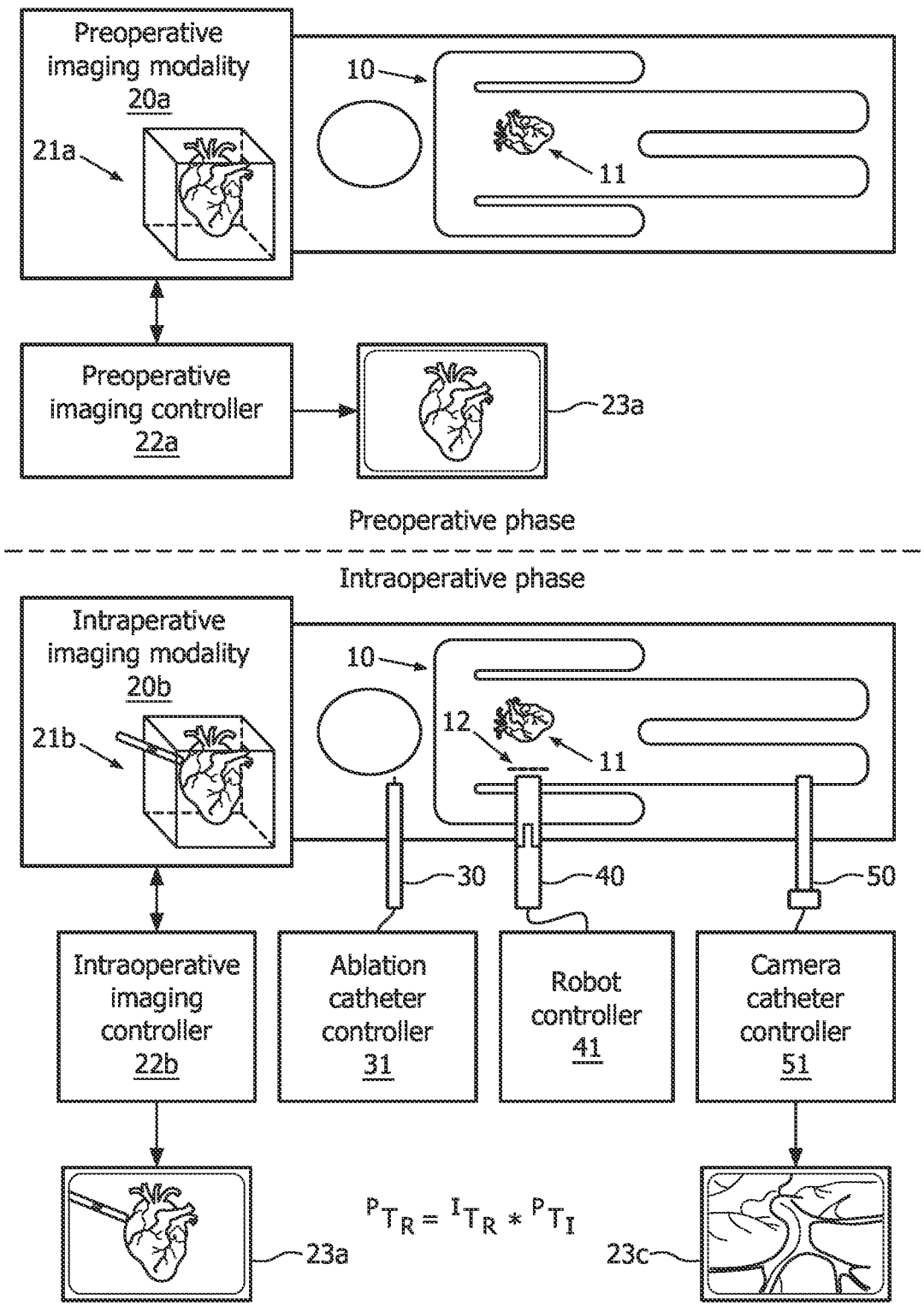
FIG. 1 illustrates an exemplary embodiment of a minimally invasive Cox-Maze procedure in accordance with the inventive principles of the present disclosure.

To facilitate an understanding of the present disclosure, the following description of FIG. 1, teaches basic inventive principles of an image guidance based autonomous control of an articulated robot 40 for performing a single-port minimally invasive Cox-Maze procedure on a patient 10 involving a treatment catheter in the form of an ablation catheter. From this description, those having ordinary skill in the art will appreciate how to apply the inventive principles of the present disclosure to various single-port minimally invasive treatment procedures incorporating image guidance based autonomous control of an articulated robot involving any type of treatment catheter.

Referring to FIG. 1, a preoperative phase of the minimally invasive Cox-Maze procedure involves a preoperative imaging controller 22a controlling a generation by a preoperative imaging modality 20a (e.g., a CT, MRI or US imaging modality) as known in the art of a preoperative image 21a illustrative of a heart 11 within a thoracic region of patient 10. During the preoperative phase, preoperative imaging controller 22a further controls a display as known in the art of preoperative image 21a of heart 11 on a monitor 23a for diagnostic purposes, particularly for delineating a planned ablation path traversing heart 11 within preoperative image 21a.

Still referring to FIG. 1, an intraoperative phase of the minimally invasive Cox-Maze procedure involves a single-port incision 12 into the thoracic region of patient 10 (e.g., between the ribs or subxypoid) whereby a robot controller 41 may autonomously control a navigation by articulated robot 40 of an ablation catheter 30 within the thoracic region of patient 10 in accordance with the preoperative planned ablation path traversing heart 11. In practice, articulated robot 40 may support a navigation of a camera catheter 50 alternatively or concurrently with ablation catheter 30.

To execute the procedural ablation of heart 10 as planned, articulated robot 40 must be registered to preoperative image 21a. To this end, articulated robot 40 supporting ablation catheter 30 (and optionally camera catheter 50) is manually or robotically inserted via a robot controller 41 within the thoracic region of patient 10 adjacent heart 11 whereby an intraoperative imaging controller 22b controls a generation by an intraoperative imaging modality 20b (e.g., an X-ray or endoscopic imaging modality) as known in the art of an intraoperative image 21b illustrative of articulated robot 40 relative to heart 11 within the thoracic region of patient 10. If camera catheter 51 is deployed via articulated robot 40, then a camera catheter controller 51 controls a display an endoscopic video view of heart 11 via camera catheter 51 on monitor 23b or an additional monitor 23c as known in the art for positioning purposes of articulated robot 40 relative to heart 11 of patient 10 and/or for registration purposes of preoperative image 21a and intraoperative image 21b.

The registration of articulated robot 40 to preoperative image 21a is accomplished by one of the controllers 22a, 22b or 41 in accordance with the following equation [1]:

$$^{P}T_{R} = {}^{I}T_{R} * {}^{P}T_{I} \quad [1]$$

where $^{I}T_{R}$ is the transformation of articulated robot 40 to intraoperative image 21b, where $^{P}T_{I}$ is the transformation of intraoperative image 21b to preoperative image 21a, and where $^{P}T_{R}$ is the transformation of articulated robot 40 to preoperative image 21a.

Figure 8:
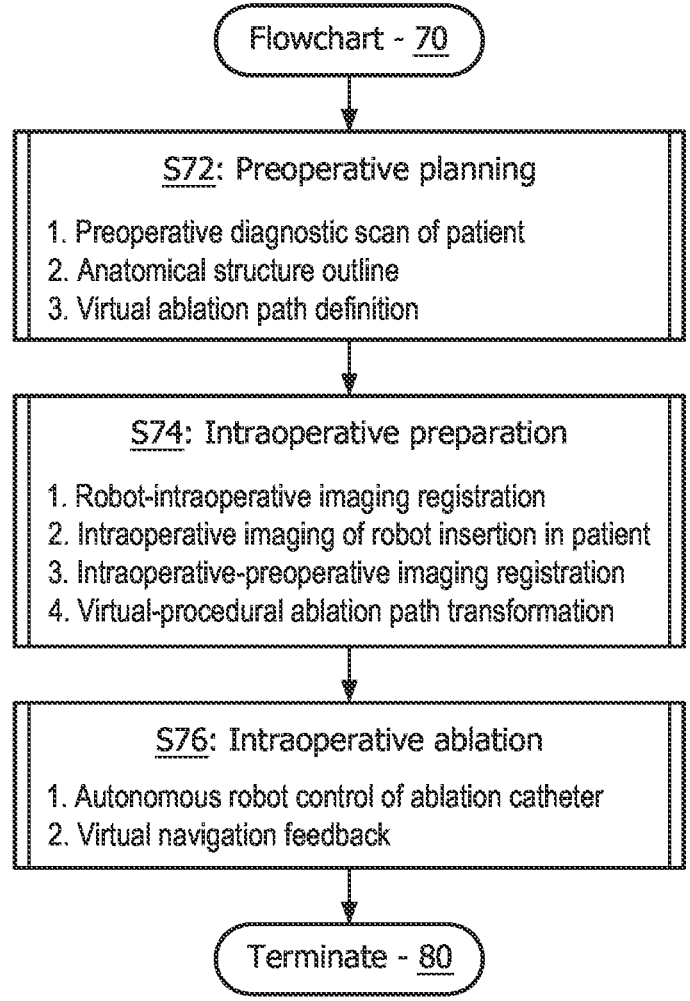
FIG. 8 illustrates a flowchart representative of an exemplary embodiment of an robotic surgical method in accordance with the inventive principles of the present disclosure.

A more detailed exemplary description of a registration of articulated robot 40 to preoperative image 21a will be provided herein with the description of FIG. 8.

Still referring to FIG. 1, upon the registration, robot controller 41 is capable of autonomously controlling a navigation by articulated robot 40 of ablation catheter 30 within the thoracic region of patient 10 in accordance with the ablation path traversing heart 11 as planned during the preoperative phase. In practice, ablation catheter 30 may be a cyroablation catheter or a thermoablation catheter whereby an appropriate energy source (not shown) is controlled by an ablation catheter controller 31 to provide ablation catheter 30 with a specified degree of energy to perform the desired ablation of heart 11 as ablation catheter 30 is traversed across 11. During the ablation, preoperative imaging controller 22a or intraoperative imaging controller 22b controls a display of a virtual navigation of ablation catheter 41 within preoperative image 21a of heart 11 as known in the art for surgical feedback purposes.

Upon completion, the execution of the Cox-Maze procedure as shown in FIG. 1 results in an ablation of heart 11 that impedes any future occurrences of an atrial fibrillation of heart 11.

In practice, preoperative imaging modality 20a and intraoperative imaging modality 20b may or may not be the same type of imaging modality.

Also in practice, the controllers of FIG. 1 may be installed within a single workstation or distributed across multiple workstations.

Figure 2A:
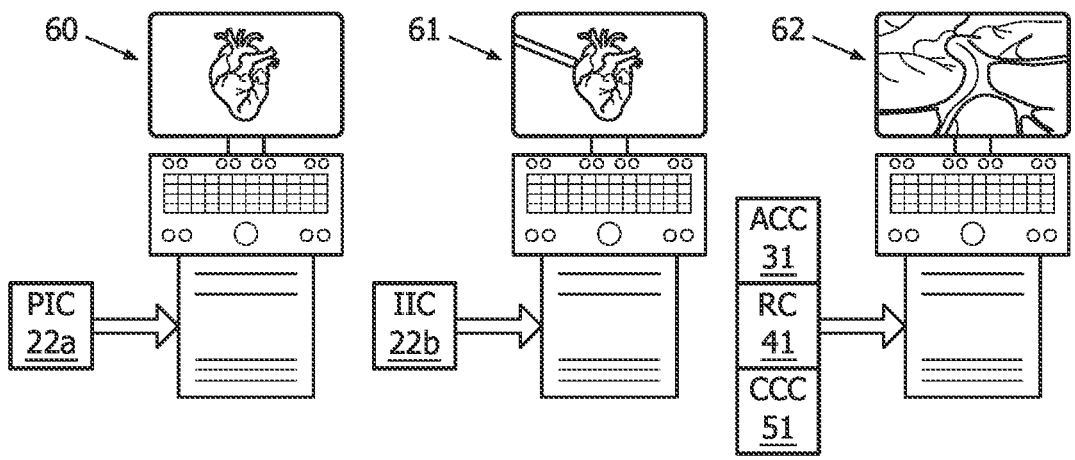
FIGS. 2A-2C illustrate exemplary embodiments of workstations in accordance with the inventive principles of the present disclosure.

For example, FIG. 2A illustrates a preoperative imaging workstation 60 having preoperative imaging controller 22a installed therein for CT, MRI or US imaging, and an intraoperative imaging workstation 61 having intraoperative imaging controller 22b installed therein for X-ray or endoscopic imaging. FIG. 2A further illustrates a surgical robot workstation 62 having ablation catheter controller 31, robot controller 41 and camera catheter controller 51 installed therein for autonomously executing the Cox-Maze procedure under image guidance.

Figure 2B:
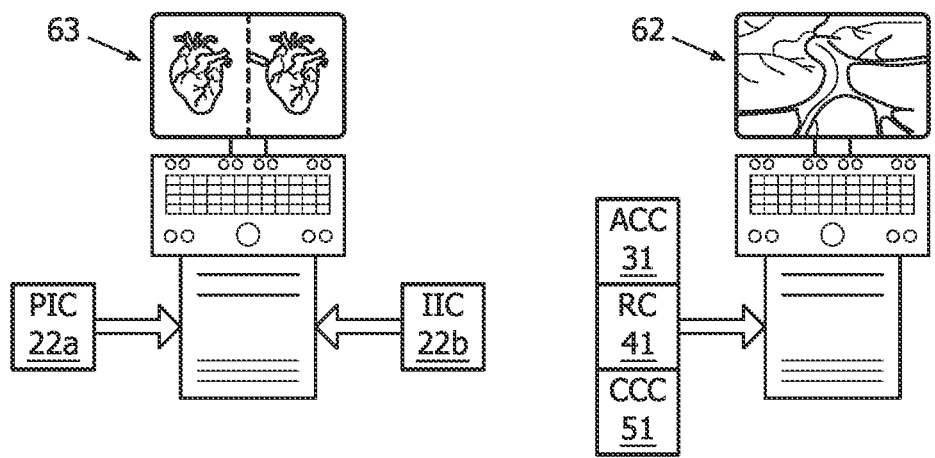

Also by example, FIG. 2B illustrates an imaging workstation 63 having both preoperative imaging controller 22a and intraoperative imaging controller 22b installed therein for the same type of imaging or different types of imaging. FIG. 2B further illustrates surgical robot workstation 62 for autonomously executing the Cox-Maze procedure under image guidance.

Figure 2C:
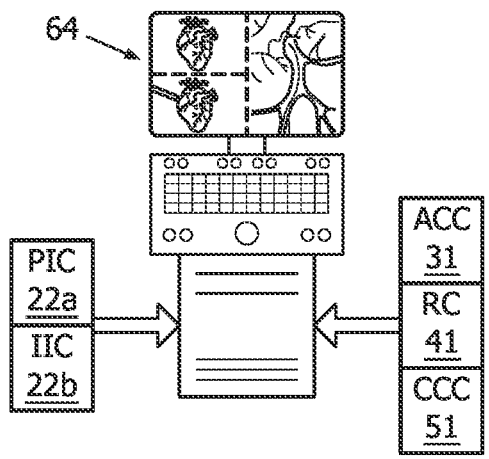

By further example, FIG. 2C illustrates a surgical workstation 64 having all controllers of FIG. 1 installed therein for the same type of imaging or different types of imaging and for autonomously executing the Cox-Maze procedure under image guidance.

To facilitate a further understanding of the present disclosure, the following description of FIGS. 3-7, teaches basic inventive principles of an articulated robot. From this description, those having ordinary skill in the art will appreciate how to apply the inventive principles of the present disclosure to any type of articulated robot suitable for a single-port minimally invasive procedure.

Generally, an articulated robot of the present disclosure employs a proximal linkage, a distal linkage and optionally one or more intermediate linkages. The articulated robot further includes joints interconnecting the linkages in a complete or partial serial arrangement, and controllable by the robot controller.

In practice, joint may be any type of pivot joint including, but not limited to, a ball and socket joint, a hinge joint, a condyloid joint, a saddle joint and a rotary joint.

Also in practice, each joint may be equipped with a motor for controlling a pose of each linkage, and/or a position sensor of any type (e.g., an encoder) for generating pose data informative of a pose (i.e., orientation and/or location) of the distal linkage relative to the proximal linkage.

Figure 3A:
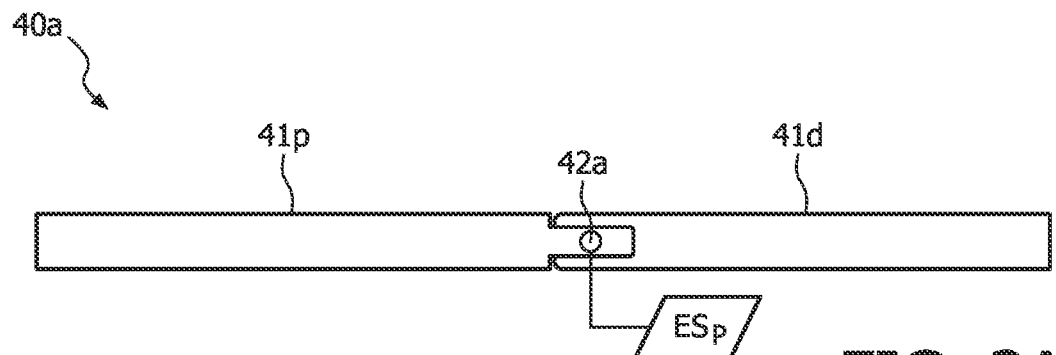
FIGS. 3A and 3B illustrate an exemplary embodiment of an articulated robot having two (2) interconnected linkages in accordance with the inventive principles of the present disclosure.
Figure 3B:
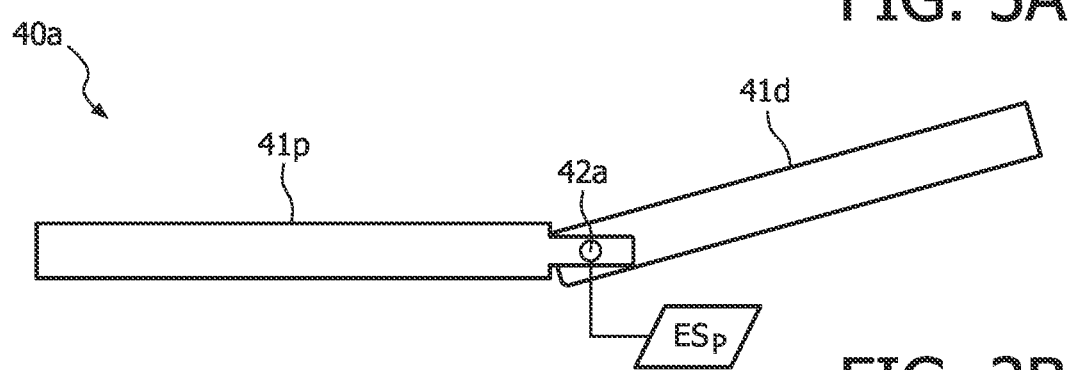

For example, referring to FIGS. 3A and 3B, an articulated robot 40a employs a proximal linkage 41p and a distal linkage 41d interconnected by a motorized pivot joint 42a equipped with a rotary encoder (not shown) to generate an encoded signal ESP informative of an angular orientation between proximal linkage 41p and distal linkage 41d. FIG. 3A illustrates a 180° angular orientation between proximal linkage 41p and distal linkage 41d, and FIG. 3B illustrates an approximate 165° angular orientation between proximal linkage 41p and distal linkage 41d. Given the single pivot joint 42a, the angular orientation between proximal linkage 41p and distal linkage 41d is informative of a pose (i.e., orientation and/or location) of distal linkage 41d relative to proximal linkage 41p.

Figure 4A:
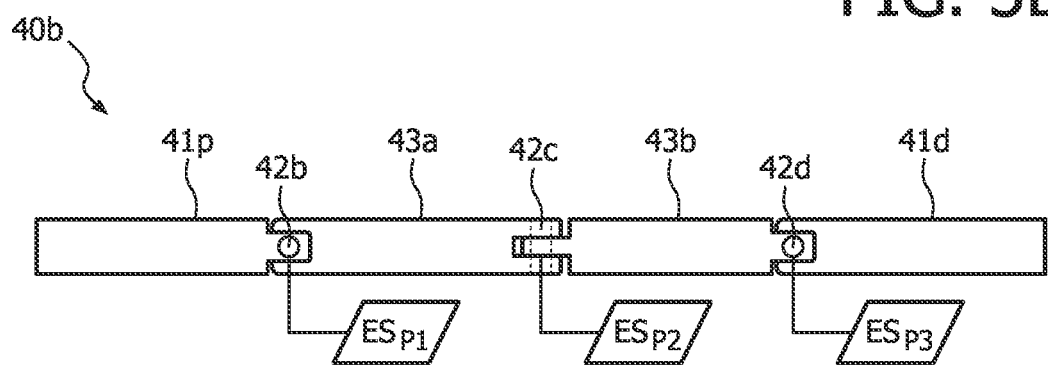
FIGS. 4A and 4B illustrate an exemplary embodiment of an articulated robot having four (4) interconnected linkages in accordance with the inventive principles of the present disclosure.
Figure 4B:
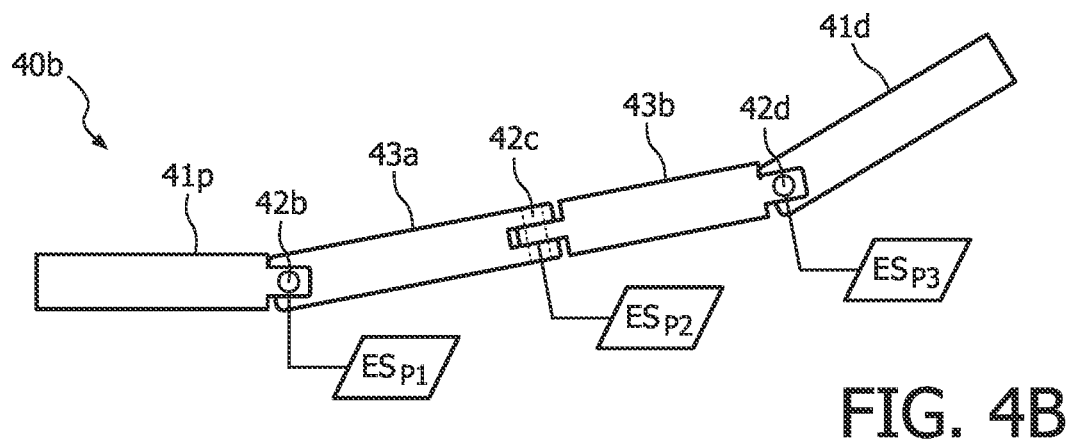

By further example, referring to FIGS. 4A and 4B, an articulated robot 40b further employs a pair of intermediate linkages 43a and 43b between proximal linkage 41p and distal linkage 41d with all linkages 41 and 43 being interconnected by motorized pivot joint 42b-42d equipped with rotary encoders (not shown) to generate encoded signals $ES_{P1}$-$ES_{P3}$ collectively informative of a pose (i.e., orientation and/or location) of distal linkage 41d relative to proximal linkage 41p.

Also in practice, an articulated art of the present disclosure may have a static connection to a robot platform for maintaining a stationary positon of the proximal linkage, or alternatively employs a pivot base, for connection to the robot platform that enables a manual or robotic control of a pivotal motion of the proximal linkage relative to the robot platform.

Figure 5A:
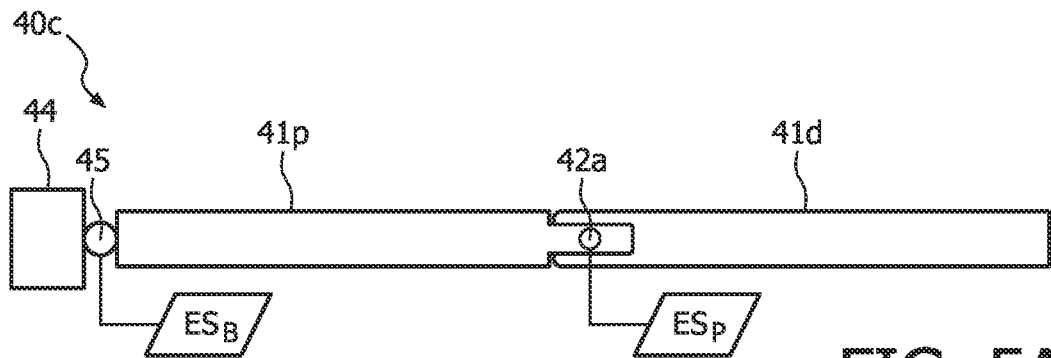
FIGS. 5A and 5B illustrate an exemplary embodiment of an articulated robot having two (2) interconnected linkages and a pivot base in accordance with the inventive principles of the present disclosure.
Figure 5B:
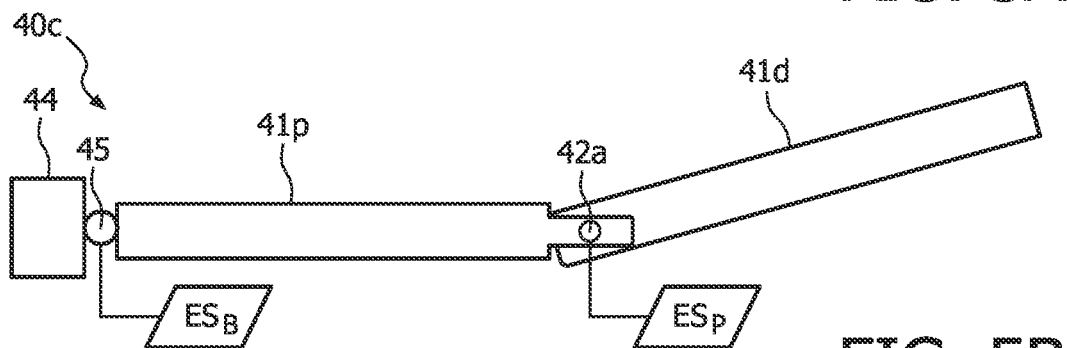

For example, referring to FIGS. 5A and 5B, an articulated robot 40c is a version of articulated robot 40a (FIGS. 3A and 3B) further employing a motorized pivot base 44 connectable to a robot platform (not shown), and connected to proximal linkage 41p by a motorized pivot joint 45 equipped with a rotary encoder (not shown) to generate an encoded signal $ES_{B}$ informative of an angular orientation between proximal linkage 41p and the robot platform.

Figure 6A:
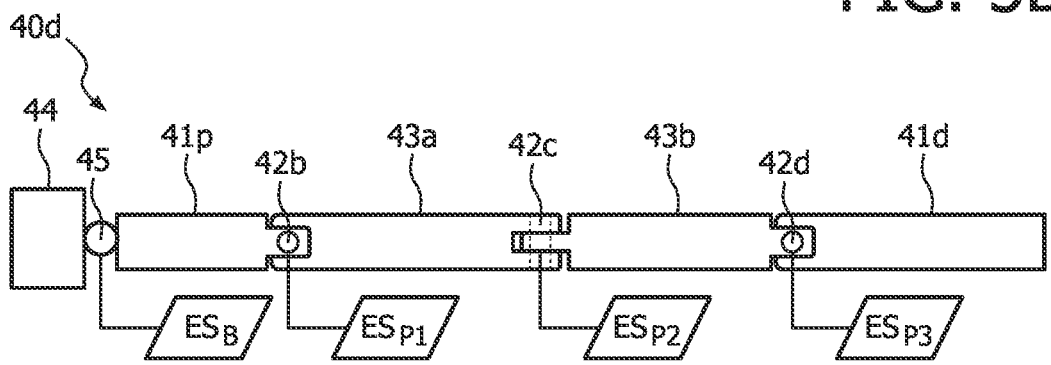
FIGS. 6A and 6B illustrate an exemplary embodiment of an articulated robot having four (4) interconnected linkages and a pivot base in accordance with the inventive principles of the present disclosure.
Figure 6B:
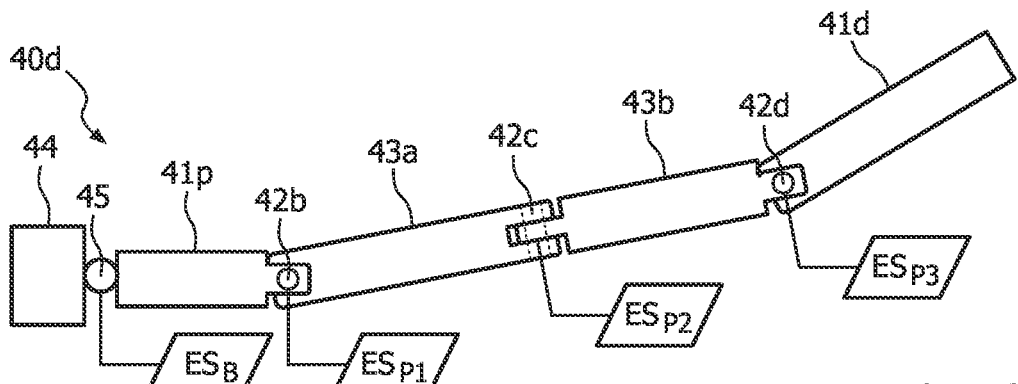

By further example, referring to FIGS. 6A and 6B, an articulated robot 40d is a version of articulated robot 40b (FIGS. 4A and 4B) further employing motorized pivot base 44 connectable to a robot platform (not shown), and connected to proximal linkage 41p by motorized pivot joint 45 equipped with a rotary encoder (not shown) to generate an encoded signal $ES_B$ informative of an angular orientation between proximal linkage 41p and the robot platform.

Also in practice, the linkages of an articulated robot of the present disclosure may be structurally designed with one or more internal and/or external channels for an ablation catheter and/or a camera catheter.

Figure 7A:
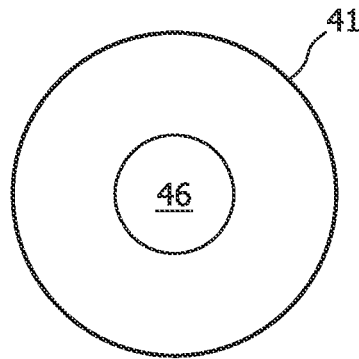
FIGS. 7A and 7B illustrate exemplary embodiments of channels within an articulated robot in accordance with the inventive principles of the present disclosure.
Figure 7B:
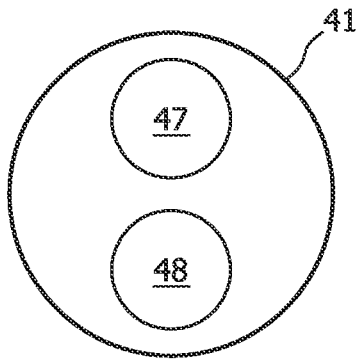

For example, FIG. 7A illustrates a single internal channel 46 extending through linkages 41 of articulated robot 40a shown in FIGS. 3A and 3B. For this channel embodiment, during the procedure, a camera catheter is first extended through channel 46 of linkages 41 and aligned with a distal tip of articulated robot 40a for imaging purposes when initially inserting articulated robot 40a within the anatomical region. Thereafter, for the ablation procedure, an ablation catheter is extended through channel 46 of linkages 41 and aligned with the distal tip of articulated robot 40a for ablation purposes as articulated robot 40a is traversed across the anatomical structure. By further example, FIG. 7B illustrates a pair of internal channels 47 and 48 extending through linkages 41 of articulated robot 40a shown in FIGS. 3A and 3B. For this channel embodiment, during the procedure, a camera catheter and an ablation catheter are simultaneously extended respectively through channels 47 and 48 for the aforementioned imaging and ablation purposes.

To facilitate a further understanding of the present disclosure, the following description of FIGS. 8 and 9, teaches basic inventive principles of a robotic surgical method of the present disclosure. From this description, those having ordinary skill in the art will appreciate how to apply the inventive principles of the present disclosure to for any type of single-port minimally invasive procedure.

Referring to FIG. 8, a flowchart 70 representative of a robotic surgical method of the present disclosure involves a stage S72 for preoperative planning, a stage S74 for intraoperative preparation and a stage S76 for intraoperative ablation.

Specifically, stage S72 of flowchart 70 encompasses a preoperative diagnostic scan of the patient, an outlining of an anatomical structure within the anatomical region, and a defining of a planned ablation path traversing the outlined anatomical structure.

For example, FIG. 1 illustrates a preoperative image 21a of a heart 11 of a patient 10 generated by a preoperative imaging modality 20a as controlled by preoperative imaging controller 22a. For stage S72, the raw data of preoperative image 21a is loaded into a path planning control module 80 as shown in FIG. 9 whereby the raw data of preoperative image 21a is converted into a 3D working model 13 of heart 11 having a rear perspective view of a superior vena cava ("SVC"), an inferior vena cava ("IVC"), mitral valve ("MV") and left atrial appendage ("LAA"), and further whereby a surgeon may interact with path planning control module 80 to define a planned ablation path symbolically shown as dashed line traversing model 13 of heart 11.

In practice, path planning control module 80 may implement any virtual planning technique known in the art that is suitable for the particular type of minimally invasive procedure being performed.

Also in practice, path planning control module 80 may be an application module of preoperative imaging controller 22a, intraoperative imaging controller 22b or robot controller 41.

Referring back to FIG. 8, a stage S74 of flowchart 70 encompasses a registration of the articulated robot to the intraoperative image, an intraoperative imaging of the articulated robot as inserted into the patient, a registration of the intraoperative-preoperative images, and a transformation of the planned ablation path into ablation path.

For example, a registration control module 81 is utilized to calculate a transformation $^{I}T_{R}$ of articulated robot 40 as held by a robot platform 90 to intraoperative image 21b. In practice, registration control module 81 may implement any known registration technique suitable for articulated robot 40.

Subsequently, articulated robot 40 is inserted within patient 10 and positioned relative to heart 11 as previously described herein to facilitate a generation of intraoperative image 21b of articulated robot 40 relative to heart 11. In particular, for X-ray imaging, multiple X-ray images are loaded into registration control module 81 for a 3D reconstruction of intraoperative image 21b to enable an identification by registration control module 81 of articulated robot 40 relative to heart 11. In practice, a distal linkage and the most distal pivot joint of articulated robot 40 should be illustrated in intraoperative image 21b to facilitate the identification of articulated robot 40 relative to heart 11.

From a heart identification within preoperative image 21a and intraoperative image 21b, registration control module 81 calculates a transformation $^{P}T_{I}$ of intraoperative image 21b to preoperative image 21a. In practice, registration control module 81 may implement any known identification/registration techniques suitable for such a registration.

Also in practice, registration control module 81 may be an application module of preoperative imaging controller 22a, intraoperative imaging controller 22b and robot controller 41, or distributed between preoperative imaging controller 22a, intraoperative imaging controller 22b and robot controller 41.

From the calculated of intraoperative image 21b to preoperative image 21a, registration control module 81 calculates a transformation $^{P}T_{R}$ of articulated robot to preoperative image 21a in accordance with the equation [1]:

$$^{P}T_{R}=^{I}T_{R}*^{P}T_{I} \quad [1]$$

Figure 9A:
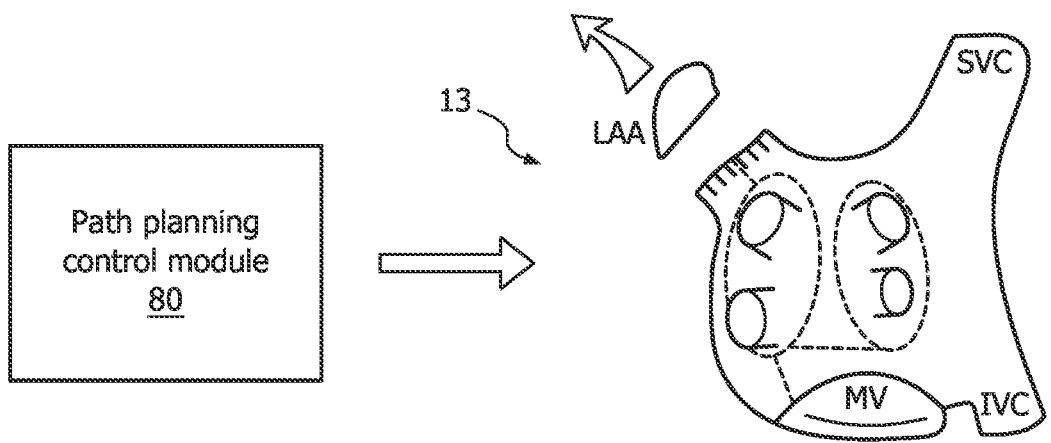
FIGS. 9A-9D illustrates an exemplary execution of the flowchart illustrated in FIG. 8.
Figure 9B:
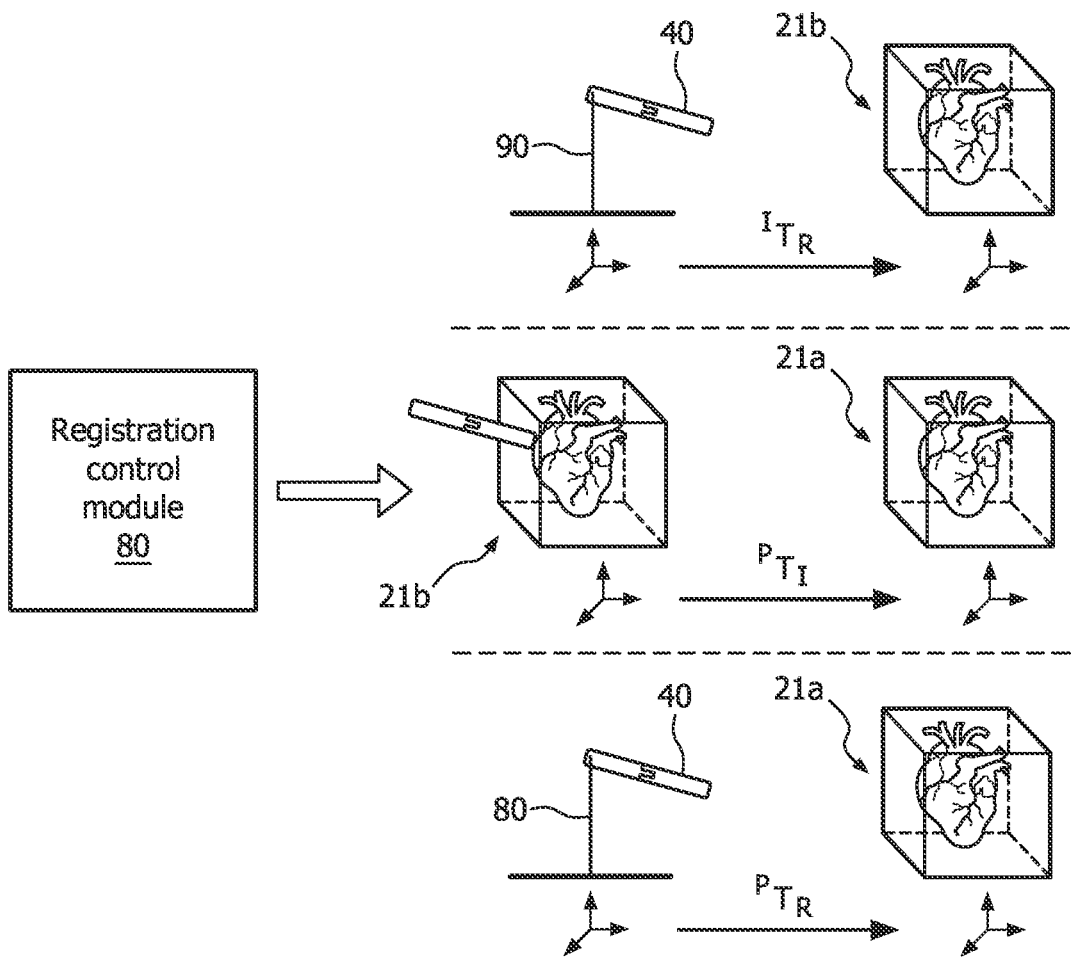
Figure 9C:
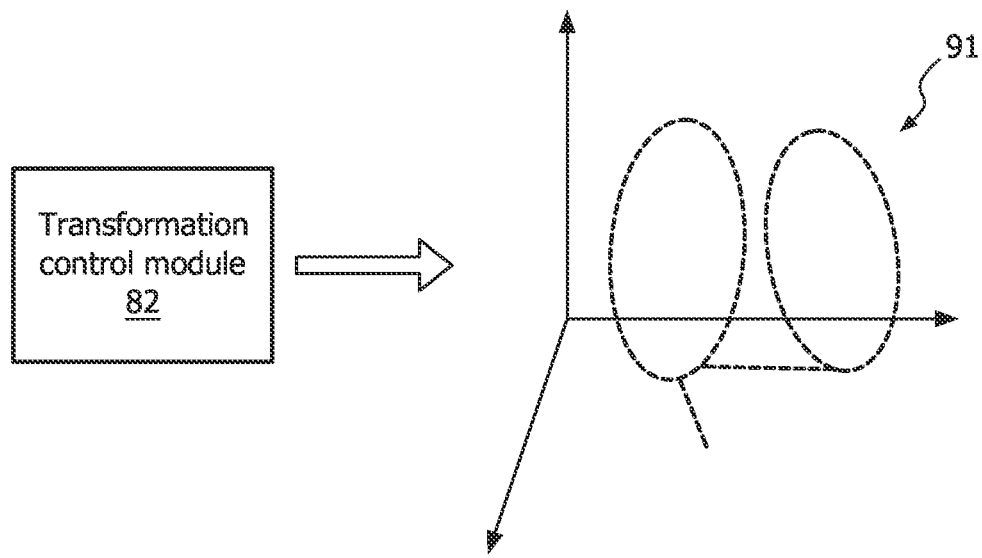
Figure 9D:
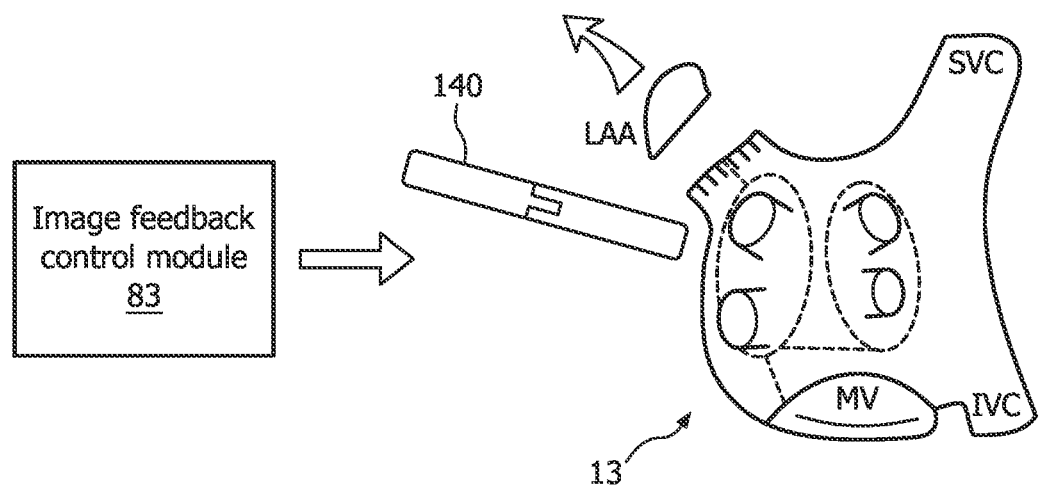

From the calculated transformation $^{P}T_{R}$ of articulated robot to preoperative image 21a, a transformation control module 82 as shown in FIG. 9C transforms the virtual planned path into a procedure path 92 within the robotic coordinate system.

In practice, transformation control module 82 may be implement any known transformation technique as known in the art suitable for articulated robot 40. Also in practice, transformation control module 82 may be an application module of preoperative imaging controller 22a, intraoperative imaging controller 22b or robot controller 41.

Referring back to FIG. 8, a stage S76 of flowchart 70 encompasses an autonomous control by the robot controller of the ablation catheter within the anatomical region based on the intraoperative ablation path of stage S74, and a display of a virtual navigation feedback of the ablation catheter traversing the anatomical structure via the intraoperative ablation path.

For example, robot controller 41 of FIG. 1 executes a servo control of the motorized pivot joints of articulated robot 40 in accordance with the intraoperative ablation path shown in FIG. 9C, and an image feedback control module 83 controls a display of a virtual articulated robot 140 traversing a working model 13 of preoperative image volume 21a.

Referring back to FIG. 8, flowchart 70 is terminated upon a completion of the path or any of the stages S72-76 may be repeated to any degree as necessary.

Referring to FIGS. 1-9, those having ordinary skill in the art will appreciate numerous benefits of the present disclosure including, but not limited to, the novel and unique robotic approach to a single port minimally invasive procedure, particularly a minimally invasive Cox-Maze procedure.

Furthermore, as one having ordinary skill in the art will appreciate in view of the teachings provided herein, features, elements, components, etc. described in the present disclosure/specification and/or depicted in the FIGS. 1-9 may be implemented in various combinations of electronic components/circuitry, hardware, executable software and executable firmware and provide functions which may be combined in a single element or multiple elements. For example, the functions of the various features, elements, components, etc. shown/illustrated/depicted in the FIGS. 1-9 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive single-port image guided minimally invasive procedures, particularly for minimally invasive Cox-Maze procedures (which embodiments are intended to be illustrative and not limiting), it is noted that modifications and variations can be made by persons having ordinary skill in the art in light of the teachings provided herein, including the FIGS. 1-9. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A robotic surgical method for executing a procedural treatment of an anatomical structure within an anatomical region, the robotic surgical method comprising:
controlling, by an imaging controller, a registration between (i) an articulated robot comprising a plurality of linkages and at least one joint interconnecting the plurality of linkages and (ii) a preoperative image illustrative of a planned treatment path within an anatomical region relative to the anatomical structure; and
controlling, by a robot controller, a navigation by the articulated robot of a treatment catheter along an intraoperative treatment path within the anatomical region relative to the anatomical structure derived from the planned treatment path within the anatomical region relative to the anatomical structure based on the registration between the articulated robot and the preoperative image, wherein at least one of the plurality of linkages and the at least one joint of the articulated robot are adapted to be inserted within the anatomical structure.

2. The robotic surgical method of claim 1, further comprising:
generating, by the articulated robot, pose data informative of a pose of a distal end of the articulated robot relative to a proximal end of the articulated robot; and
responsive to the generation of the pose data, controlling, by the robot controller, the navigation by the articulated robot of the treatment catheter along the intraoperative treatment path within the anatomical region relative to the anatomical structure.

3. The robotic surgical method of claim 1, further comprising:
controlling, by a registration controller, an image registration between the preoperative image and an intraoperative image registered to the articulated robot,
wherein the image registration includes a delineation of the anatomical structure as illustrated within the preoperative image and the intraoperative image.

4. The robotic surgical method of claim 1, further comprising:
controlling, by a path planning controller, a delineation of the planned treatment path within the anatomical region relative to the anatomical structure within the preoperative image; and
controlling, by a transformation controller, a transformation of the planned treatment path within the anatomical structure relative to the anatomical structure as illustrated within the preoperative image into the intraoperative treatment path within the anatomical region relative to the anatomical structure.

5. The robotic surgical method of claim 1, further comprising:
responsive to the control by the robot controller of the navigation, controlling, by an image feedback controller, a display within the preoperative image of a virtual navigation by the articulated robot of the treatment catheter along the planned treatment path within the anatomical region relative to the anatomical structure.

6. The robotic surgical method of claim 1, wherein the treatment catheter is one of a thermoablation catheter or a cyroablation catheter.

7. The robotic surgical method of claim 1, further comprising:
controlling, by the robot controller, simultaneous navigation by the articulated robot of the treatment catheter and a camera catheter along the intraoperative treatment path within the anatomical region relative to the anatomical structure.

8. The robotic surgical method of claim 1, further comprising:
controlling, by the robot controller, alternative navigation by the articulated robot of the treatment catheter and a camera catheter along the intraoperative treatment path within the anatomical region relative to the anatomical structure.

9. The robotic surgical method of claim 1, wherein the plurality of linkages comprises a proximal linkage and a distal linkage.

10. The robotic surgical method of claim 9, wherein the plurality of linkages further comprises at least one intermediate linkage between the proximal linkage and the distal linkage.

11. The robotic surgical method of claim 9, wherein the articulated robot further comprises a pivot base connected to the proximal linkage.

12. The robotic surgical method of claim 11, further comprising:
generating, by the articulated robot, pose data informative of a pose of a distal end of the articulated robot relative to the pivot base; and
responsive to the generation of the pose data, controlling, by the robot controller, the navigation by the articulated robot of the treatment catheter along the intraoperative treatment path within the anatomical region relative to the anatomical structure.

13. The robotic surgical method of claim 9, further comprising:
generating, by the articulated robot, pose data informative of a pose of a distal end of the articulated robot relative to the proximal linkage; and
responsive to the generation of the pose data, controlling, by the robot controller, the navigation by the articulated robot of the treatment catheter along the intraoperative treatment path within the anatomical region relative to the anatomical structure.

* * * * *